(12) United States Patent
Wills et al.

(10) Patent No.: US 12,098,752 B2
(45) Date of Patent: *Sep. 24, 2024

(54) SURGICAL TOOL

(71) Applicant: Encore Medical, L.P., Austin, TX (US)

(72) Inventors: Kevin Michael Wills, Austin, TX (US); Adam Shallenberg, Austin, TX (US)

(73) Assignee: Encore Medical, L.P., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/192,177

(22) Filed: Mar. 29, 2023

(65) Prior Publication Data

US 2023/0304536 A1 Sep. 28, 2023

Related U.S. Application Data

(63) Continuation of application No. 16/748,276, filed on Jan. 21, 2020, now Pat. No. 11,639,740.
(Continued)

(51) Int. Cl.
*F16D 3/221* (2006.01)
*A61B 17/16* (2006.01)
(Continued)

(52) U.S. Cl.
CPC .......... *F16D 3/221* (2013.01); *A61B 17/1631* (2013.01); *B25J 9/0063* (2013.01);
(Continued)

(58) Field of Classification Search
CPC ... F16D 3/221; F16D 3/2052; A61B 17/1631; A61B 17/8875; A61B 2017/0069; B25J 9/0063; Y10T 403/32811
See application file for complete search history.

(56) References Cited

U.S. PATENT DOCUMENTS

| 148,382 A | 3/1874 | Pitcher |
| 4,065,941 A | 1/1978 | Aoki |

(Continued)

FOREIGN PATENT DOCUMENTS

| EP | 3 241 506 | 11/2017 |
| EP | 2 413 818 | 12/2017 |

(Continued)

OTHER PUBLICATIONS

International Search Report and Written Opinion dated Apr. 7, 2020, in PCT-US2020-14555.

*Primary Examiner* — Greg Binda
(74) *Attorney, Agent, or Firm* — KNOBBE, MARTENS, OLSON & BEAR LLP

(57) ABSTRACT

A surgical tool including a socket having a housing and an aperture within the housing, the socket configured to receive a ball and a pin at least partially in the aperture. The ball is positioned at least partially in the socket and configured to rotate within the socket, the ball comprising an elongated opening extending through the ball. The pin is coupled to the socket and disposed at least partially in the socket on opposite sides of the socket, the pin including a first longitudinal axis and extending through the elongated opening of the ball between opposite sides of the socket. The ball is configured to partially rotate about the first longitudinal axis of the pin, and partially rotate, about a second axis perpendicular to the first longitudinal axis of the pin, in a plane aligned with the elongated opening.

18 Claims, 7 Drawing Sheets

Related U.S. Application Data

(60) Provisional application No. 62/797,101, filed on Jan. 25, 2019.

(51) Int. Cl.
*B25J 9/00* (2006.01)
*F16D 3/205* (2006.01)
*A61B 17/00* (2006.01)
*A61B 17/88* (2006.01)

(52) U.S. Cl.
CPC .... *F16D 3/2052* (2013.01); *A61B 2017/0069* (2013.01); *A61B 17/8875* (2013.01); *Y10T 403/32811* (2015.01)

(56) References Cited

U.S. PATENT DOCUMENTS

| | | |
|---|---|---|
| 4,114,401 A | 9/1978 | Van Hoose |
| 5,236,289 A | 8/1993 | Salyer |
| 6,386,074 B1 | 5/2002 | Yang |
| 8,192,103 B2 | 6/2012 | Tsai |
| 9,080,611 B2 | 7/2015 | Sander |
| 9,597,093 B2 | 3/2017 | McClymont et al. |
| 11,639,740 B2 * | 5/2023 | Wills ............ F16D 3/221 606/1 |
| 2010/0166495 A1 | 7/2010 | Tsai |
| 2017/0211632 A1 | 7/2017 | Sweewood et al. |
| 2017/0254365 A1 | 9/2017 | Chen |
| 2017/0319205 A1 | 11/2017 | Beardsley |
| 2018/0049753 A1 | 2/2018 | Chenaux et al. |
| 2018/0125536 A1 | 5/2018 | Potash et al. |
| 2018/0147069 A9 | 5/2018 | Chenaux |
| 2018/0206857 A1 | 7/2018 | Chenaux et al. |
| 2018/0250004 A1 | 9/2018 | Williams et al. |
| 2018/0250005 A1 | 9/2018 | Beardsley |
| 2018/0283460 A1 | 10/2018 | Lock |

FOREIGN PATENT DOCUMENTS

| | | |
|---|---|---|
| EP | 3 369 384 | 9/2018 |
| EP | 3 369 386 | 9/2018 |
| EP | 3 203 942 | 12/2018 |
| FR | 638719 | 6/1928 |
| WO | WO 17-029546 | 2/2017 |
| WO | WO 17-120321 | 7/2017 |
| WO | WO 18-033788 | 2/2018 |
| WO | WO 18-183202 | 10/2018 |

* cited by examiner

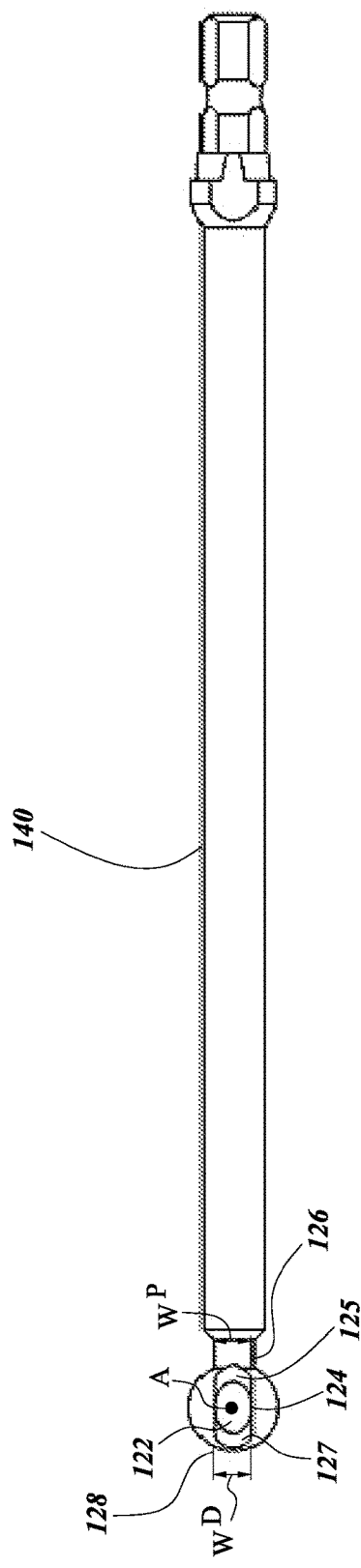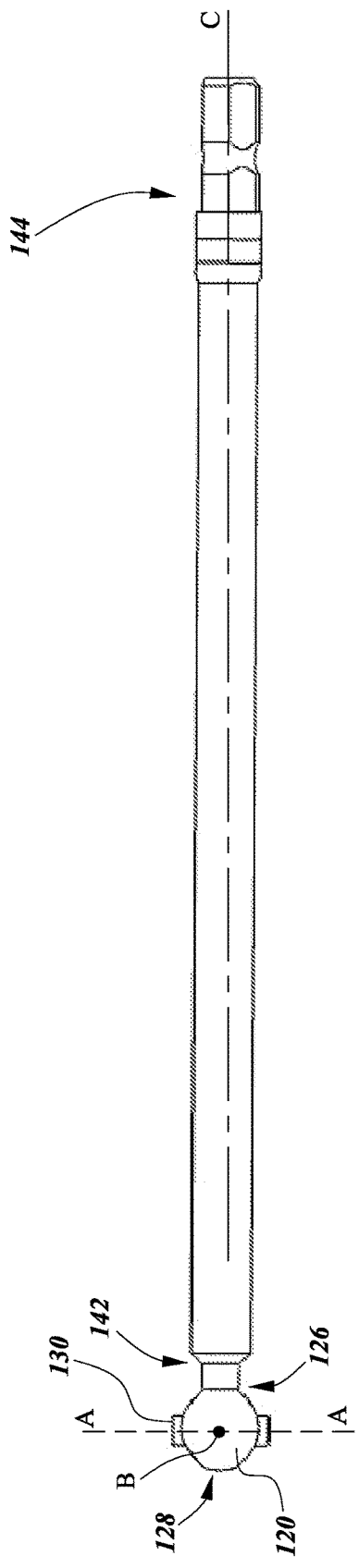
FIG. 4A
FIG. 4B

SURGICAL TOOL

REFERENCE TO PRIORITY APPLICATIONS

This application is a continuation of U.S. application Ser. No. 16/748,276 filed Jan. 21, 2020, now U.S. Ser. No. 11/639,740B2, which claims the benefit of U.S. Provisional Application No. 62/797,101 filed on Jan. 25, 2019, and titled "UNIVERSAL JOINT ASSEMBLY." The entire disclosure of each of the above items is hereby made part of this specification as if set forth fully herein and incorporated by reference for all purposes, for all that it contains.

Any and all applications for which a foreign or domestic priority claim is identified in the Application Data Sheet as filed with the present application are hereby incorporated by reference under 37 CFR 1.57.

TECHNICAL FIELD

The present disclosure relates to an assembly that allows movement of two coupled members in along various axis of rotation. More specifically, this disclosure relates to features of a universal joint assembly with a ball and socket configuration.

BACKGROUND

A background is provided for introductory purposes and to aid the reader in understanding the detailed description. The background should not be taken as an admission of any prior art to the claims.

Universal joint assemblies are used in the medical field for various tools, including surgical tools. Universal joint assemblies may be used to adjust the configuration of the surgical tool so that the surgical tool can be used at various angles.

SUMMARY

The devices, systems, and methods of the present disclosure have several features, no single one of which is solely responsible for its desirable attributes. Without limiting the scope of this invention as expressed by the claims which follow, certain innovations will now be discussed briefly. After considering this discussion, and other section provided herein, one will understand how the features of this disclosure provide several advantages over other universal joint assemblies.

Universal joint assemblies are used in the medical field for various tools, including surgical tools. Universal joint assemblies may be used to adjust the configuration of the surgical tool so that the surgical tool can be used at various angles.

One innovation includes a device, comprising a socket having a housing and an aperture within the housing, the socket configured to receive a ball and a pin at least partially in the aperture, the ball disposed at least partially in the socket and configured to rotate within the socket, the ball comprising an elongated opening extending through the ball, and the pin coupled to the socket and disposed at least partially in the socket, the pin comprising a first longitudinal axis and extending through the elongated opening of the ball between opposite sides of the socket. According to various embodiments, the ball is to be configured to partially rotate about the first longitudinal axis of the pin, and partially rotate, about a second axis perpendicular to the first longitudinal axis of the pin, in a plane aligned with the elongated opening. The embodiments of the device, including those illustrated and described herein, can have many other aspects (or features), or fewer aspects. In one aspect, the device further includes an elastic mechanism biased to exert a force on the ball in at least one direction. The elastic mechanism may include one or more components. In some embodiments, a component of the elastic mechanism contacts a surface of the ball. In some embodiments, the elastic mechanism is coupled to the socket. In some embodiments, the elastic mechanism comprises a spring. In some embodiments, the elastic mechanism is configured to exert a bias force on the ball in a direction along a longitudinal axis of the device in a direction from the elastic mechanism towards the ball. In some embodiments, the elongated opening has a width and a length, and the width is equal to or greater than the diameter of the pin. In some embodiments, the elongated opening extends from a first surface of the ball to a second surface of the ball opposite the first surface.

One innovation includes a universal joint that has a socket, ball, and a pin. The socket is configured to receive the ball and the pin. The ball is configured to rotate within the socket. The ball has an opening extending therethrough. The opening may be elongated, larger in a length dimension than in a width dimension. The pin couples to the socket. The pin has a first longitudinal axis and extends through the opening of the ball between opposite sides of the socket. The ball is configured to rotate about the first longitudinal axis of the pin and a second axis perpendicular to the first long axis of the pin.

Another aspect is a drive shaft coupled to the ball. The drive shaft has a third longitudinal axis and is configured to rotate about the third longitudinal axis. In some embodiments, the third longitudinal axis of the drive shaft is perpendicular to a plane defined by the first longitudinal axis of the pin and the second axis.

Another aspect is a fitting coupled to the socket. The fitting has a fourth longitudinal axis and is configured to rotate about the fourth longitudinal axis of the fitting. In some embodiments, the fitting is a quick connect fitting configured to couple to a tool. In some embodiments, the fitting is a surgical drill bit or surgical screw driver.

Another aspect is an elastic mechanism coupled to the socket. The elastic mechanism is biased to exert a pressure on the ball in at least one direction. In some embodiments, the elastic mechanism is a spring.

Another aspect is a universal joint that has a drive shaft coupled to the ball and a fitting coupled to the socket. The drive shaft comprising a third longitudinal axis the fitting comprising a fourth longitudinal axis. The fitting is configured to rotate about its fourth longitudinal due to rotation of the drive shaft about its third longitudinal axis. In some embodiments, the drive shaft is rigid. In some embodiments, the exterior surface of drive shaft is smooth. In some embodiments, the drive shaft is integral with the ball. A rotation of the drive shaft about the first longitudinal axis of the pin moves the drive shaft from a first position and a second position. A rotation of the drive shaft about the second axis moves the drive shaft from a third position to a fourth position.

Another innovation is a surgical tool that has a universal joint, a drive shaft, and a driver-end. The universal joint has a first joint member and a second joint member. The second joint member is configured to rotate with respect to the first joint member about a first axis and a second axis, the second axis perpendicular to the first axis. The drive shaft is coupled to the second joint member and configured to rotate about a third axis extending perpendicular to a plane formed by the first axis and the second axis. The driver-end is coupled to the first joint member. A rotation of the drive shaft about the third axis causes a rotation of the driver-end about a fourth longitudinal axis of the driver-end. The second joint member is generally spherical and the first joint member is configured to receive the second joint member. In some embodiments, the drive shaft is integral with the second joint member. In some embodiments, the drive shaft is rigid.

Another innovation is a method of adjusting a surgical tool. The surgical tool has a universal joint, a drive shaft, and a driver-end. The universal joint comprises a first joint member and a second joint member configured to rotate with respect to the first joint member about a first axis and a second axis, the second axis perpendicular to the first axis. The drive shaft is coupled to the second joint member and configured to rotate about a third axis extending perpendicular to a plane formed by the first axis and the second axis. The driver-end is coupled to the first joint member. The driver-end has a fourth longitudinal axis. A rotation of the drive shaft about the third axis causes a rotation of the driver-end about its fourth longitudinal axis. The method includes rotating the second joint member about the first axis to a first position. The driver-end and the drive shaft define a first angle in a plane defined by the second axis and the third axis. The method may include rotating the second joint member about the second axis to a second position. The driver-end and the drive shaft define a second angle in a plane defined by the first axis and the third axis. The method may include securing the second joint member in the first or second position. The method of securing the second joint member may include positioning a spring biased to exert a force on the second joint member.

BRIEF DESCRIPTION OF THE DRAWINGS

The features and advantages of the devices and methods described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. In some instances, the drawings may not be drawn to scale.

FIG. 2A depicts the universal joint in one position, and FIG. 2B depicts the universal joint in another position where a component of the universal joint is rotated about an axis that is perpendicular to a longitudinal axis of the pin (e.g., longitudinal axis A as shown in FIG. 4).

FIG. 3A depicts the universal joint in one position, and FIG. 3B depicts the universal joint in another position where a component of the universal joint is rotated about a longitudinal axis of the pin (e.g., longitudinal axis A as shown in FIG. 4).

FIG. 4A depicts a top view of a ball, drive shaft, and pin in accordance with an illustrative embodiment.

FIG. 4B depicts a front view of a ball, drive shaft, and pin in accordance with an illustrative embodiment.

DETAILED DESCRIPTION OF CERTAIN INVENTIVE ASPECTS

Figure 1:
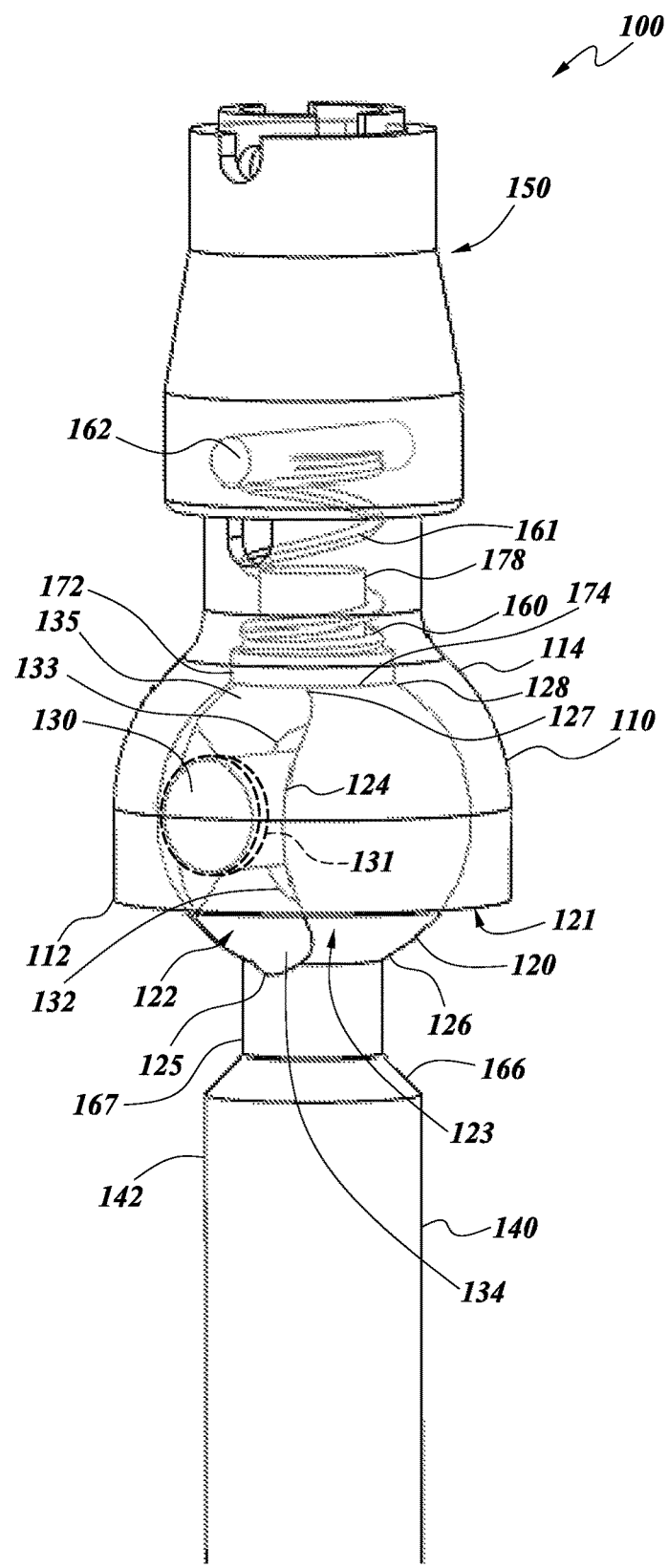
FIG. 1 depicts a perspective view of a universal joint with some parts transparent in accordance with an illustrative embodiment.

The following detailed description is directed to certain specific embodiments of the invention. However, the invention can be embodied in a multitude of different ways. It should be apparent that the aspects herein may be embodied in a wide variety of forms and that any specific structure, function, or both being disclosed herein is merely representative of one or more embodiments of the invention. An aspect disclosed herein may be implemented independently of any other aspects and that two or more of these aspects may be combined in various ways. For example, a device may be implemented, or a method may be practiced, using any number of the aspects set forth herein. In addition, such an apparatus may be implemented or such a method may be practiced using other structure, functionality, or structure and functionality in addition to, or other than one or more of the aspects set forth herein.

A damaged hip joint can cause pain and decreased mobility and may necessitate hip replacement surgery. Hip replacement surgery involves removal of at least part of a hip joint and replacement with a prosthetic implant. In a total hip replacement surgery, both the femoral head and the acetabulum of the damaged hip joint are replaced. An acetabular cup implant is attached to the acetabulum following removal of undesired portions. The femoral head implant includes a femoral head component that connects to a femoral stem component. The femoral head implant may be secured to the femur by introduction of the femoral stem component into a femoral canal. The femoral head component is positioned to engage the acetabular cup implant.

In some circumstances, bone screws are used to hold the acetabular cup implant in place, for instance, when there is insufficient bony coverage or osteoporotic bone. crew placement depends on the anatomy and health of the patient. Screws are placed carefully to avoid surrounding nerves, arteries, and veins. Screws are typically placed through strong bone. Often times, pilot holes for bone screws are drilled in the acetabulum. Surgical tools are used to drill the pilot holes and place the screws. Drilling eccentrically may affect placement of an acetabular liner in the acetabular cup. The pilot hole placement and the screw placement may be obscured and difficult to access with a linear surgical tool. A surgical tool may need to be angled in order to properly drill the pilot holes or place the screws. Certain aspects of the universal joint assembly described herein allow for a surgical tool to be configured to access difficult areas.

The surgical tools may be powered by electric motors, subjecting the tool to high RPMs. Certain aspects of the universal joint assembly described herein allow for a surgical tool to be powered by an electric motor and be configured to access difficult areas. The drive shaft used with the universal joint may be rigid. A rigid drive shaft may provide more control than a flexible drive shaft. The drive shaft may be smooth. A smooth drive shaft reduces the risk that the drive shaft may catch or damage soft tissue during surgery. At least these aspects allow the drive shaft to be run at high RPMs. The drive shaft may be driven by a surgical power gun.

The universal joint may include a socket in communication with a ball configured to roll within the socket. The ball may be coupled to the socket via a pin extending between opposite sides of the socket and through an opening extending through the ball. The opening may be elongated, as illustrated in the embodiments shown herein. The opening of the ball may be shaped and sized to allow for rotation of the ball about a longitudinal axis of the pin and about an axis extending perpendicular to the longitudinal axis of the pin. The ball may rotate about a center point where the two axes intersect.

The universal joint may connect a drive shaft to a driver-end. The driver-end may be a surgical tool, such as a drill bit, screw driving feature, modular connection, quick-connect fitting, etc. The universal joint allows for rotation of the driver-end while the driver-end is oriented at an angle to the drive shaft. The universal joint may also allow for the angle of the driver-end to be adjusted to different angles with respect to the drive shaft in at least two dimensions. The drive shaft may be configured to rotate about its longitudinal axis, which may be perpendicular to a plane defined by the longitudinal axis of the pin and the axis perpendicular to the longitudinal axis of the pin. Rotation of the drive shaft may cause rotation of the socket coupled to the drive shaft, and consequently rotation of the pin, which may cause rotation of the driver-end about its long axis. In other words, the pin may transmit torque between the socket and the sphere to rotate the driver-end.

The universal joint may optionally include a spring biased to exert pressure on the ball in at least one direction. The spring may maintain a position of the ball within the socket after adjustment of the ball to a desired configuration.

The following is a list of certain components that are described and enumerated in this disclosure in reference to the above-listed figures. However, any aspect of the devices illustrated in the figures, whether or not named out separately herein, can form a portion of various embodiments of the invention and may provide basis for claim limitation relating to such aspects, with or without additional description. The enumerated components include:

100 universal joint assembly
110 socket (housing)
112 open end
114 closed end of socket
120 ball
121 aperture
122 opening, elongated generally in-line with drive shaft
123 exterior surface of ball
124 edge of opening on surface of ball
125 proximal edge of opening on surface of ball
126 proximal end of ball
127 distal edge of opening on surface of ball
128 distal end of ball, adjacent to surface 174 of contact component
130 pin
131 recess
132 proximal inner portion of inside surface of ball opening
133 distal inner portion of inside surface of ball opening
134 proximal outer portion of inside surface of ball opening
135 distal outer portion of inside surface of ball opening
140 first portion drive shaft
142 drive shaft
144 proximal end of drive shaft
150 fitting
152 inner component
154 outer component
160 elastic (biasing) mechanism
161 spring
162 pin
163 first edge of housing
164 second edge of housing, opposite first edge
166 tapered portion of drive shaft
167 second narrowed portion drive shaft
168 distal end of driveshaft
170 angle indicator showing the amount the housing surrounds the ball
171a first side of indicator
171b second side of indicator
172 contact component of elastic mechanism
174 surface of contact component 172 that contacts surface of ball 120
176 spring contact surface of contact component 172
178 narrow elongated center portion of contact component 172

FIG. 1 depicts an example of a universal joint assembly 100, in accordance with some embodiments, with portions transparent to see underlying structures. The universal joint assembly 100, includes a socket (or housing) 110 having an open end 112 and a closed end 114. The socket 110 is configured to receive a ball 120 through the open end 112 of the socket 110. The socket 110 includes an aperture 121 which is accessed through the open end 112, the ball 120 being at least partially disposed in the aperture 121 of the socket 110. The ball 120 has an exterior surface 123 that is adjacent to the socket 110.

The ball 120 includes an opening (or elongated opening) 122 in the exterior surface 123, the opening extending through the ball from one side of the ball 120 to the opposite side of the ball 120. As illustrated in FIG. 1, the opening 122 has an edge 124 around the perimeter of the opening 122 on the surface of the ball 120. The elongated opening 122 has a shorter direction and a longer direction. In the example illustrated in FIG. 1, in the longer direction the elongated opening 122 can be aligned with a longitudinal axis of the first portion of the drive shaft 140. In the longer direction of the elongated opening 122, the edge 124 extends from a proximal edge of the opening 125 to a distal edge of the opening 127. In some embodiments, the opening 122 extends through the ball 120 such that it has an equal cross-section along the extent of the opening from either side of the middle of the opening (in the center of the ball 120) to the edge 124. In some embodiments including the illustrated embodiment, the opening 122 has a smaller cross-sectional area interior to the ball 120 relative to the cross-sectional area at the surface of the ball 120, e.g., along edge 124.

In some embodiments, the opening 122 has a smallest cross-sectional area in the center of the ball 120. A pin 130 extending through the opening 122 can be coupled to opposite portions of the inside of the socket 110. The two ends of the pin 130 can contact the socket 110 and hold the pin, and the ball, in the socket 110. The pin 130 may be cylindrically-shaped. At least a portion of the surface of the pin 130 (e.g., the cylindrical surface) may contact a portion of an inside surface of the ball. For example, the pin 130 may contact a proximal inner portion 132 of the inside surface of the ball 130, and/or the pin 130 may contact a distal inner portion 133 of the inside surface of the ball 130. The elongated opening 122, and the wider width of the opening 122 on the outer portion of the ball allows movement of the ball 120 (and correspondingly the drive shaft 142) relative to the pin 130 in a direction such that in a first position the pin 130 is positioned near the proximal edge 125 of the opening on the surface of the ball, and in a second position the pin 130 is positioned near the distal edge 127 of the opening 122 on the surface of the ball 120.

In some embodiments, the cross-sectional area of the opening 122 decreases as the opening 122 extends from the outside surface 123 of the ball 120 to a center portion of the ball 120, and then the cross-sectional area increases as the opening 122 continues to extend from the center portion of the ball 120 to the surface 123 of the ball 120. The opening 122 has a surface interior to the ball 120 comprising a proximal outer portion 134 of the inside surface that begins at the edge 124, and a proximal inner portion 132 of the inside surface at the center of the ball 120. The proximal and distal inner portions 134, 132 may be planar or curved. In the example illustrated in FIG. 1, both of the sides of the opening extend towards the drive shaft portion and the biasing mechanism 160 on both sides of the ball 120. A portion of the opening is wider at the outside of the ball 120 than at the inside of the ball 120 where a pin 130 is positioned through the opening 122 and contacts a surface of the ball 120 on an inner portion of the ball 120. The opening 122 may be symmetrically aligned on the ball 120, or asymmetrically aligned. For example, as illustrated in FIG. 1, the opening 122 is symmetrically aligned on the ball 120 extending from the proximal edge of the opening 125 near the proximal end 126 of the ball 120, to the distal edge 127 of the opening 122 near the distal end 128 of the ball 120. In some embodiments, the opening may extend towards one end of the ball farther than the other end of the ball. For example, in some embodiments, the opening 122 may extend farther towards the proximal end 126 of the ball 120 than it extends towards the distal end 128 of the ball 120. In other embodiments, the opening 122 may extend farther towards the distal end 128 of the ball 120 than it extends towards the proximal end 126 of the ball 120.

The universal joint assembly 100 includes the pin 130 extending through the opening 122 in the ball 120. The pin 130 may be cylindrical-shaped. In some embodiments, each end of the pin 130 fits into a corresponding recess 131 in the socket 110, the recesses 131 being disposed on opposite sides of the aperture 121. For example, each recess 131 is on an interior surface of the socket 110 facing the aperture 121. The pin 130 is sized to have a cross-section that is smaller than the cross-section of the opening 122. The pin 130, socket 110, ball 120 and opening 122 are configured such that in operation, when the ball 120 is moved in the socket 110, the pin 130 and the ball 120 move relative to each other, such that the pin 130 may be positioned in any position in the opening 122, for example, such that the pin 130 is adjacent to the proximal edge 125 of the opening 122, or the pin 130 is adjacent to the distal edge 127 of the opening 122, or anywhere in between.

In some embodiments, a drive shaft 140 coupled to the ball 120, a fitting 150 coupled to the socket 110, and an elastic mechanism 160. Reference to a "universal joint assembly" as used herein generally refers to at least two components, for example, a universal joint assembly referred to herein may include the socket 110, ball 120, and pin 130. In another example, a universal joint assembly as referred to herein may include the socket 110, ball 120, pin 130, drive shaft 140, and fitting 150.

Figure 2A:
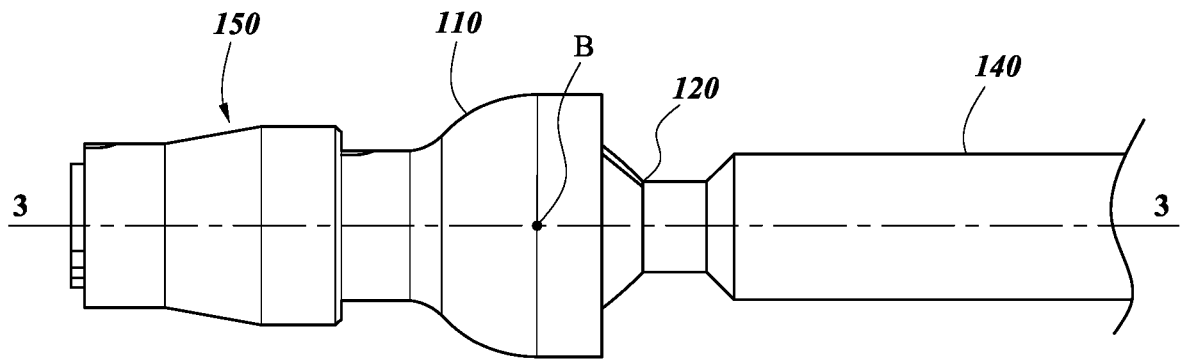
FIGS. 2A and 2B depict front views of the universal joint, with the pin extending top to bottom, in accordance with an illustrative embodiment, where
Figure 3A:
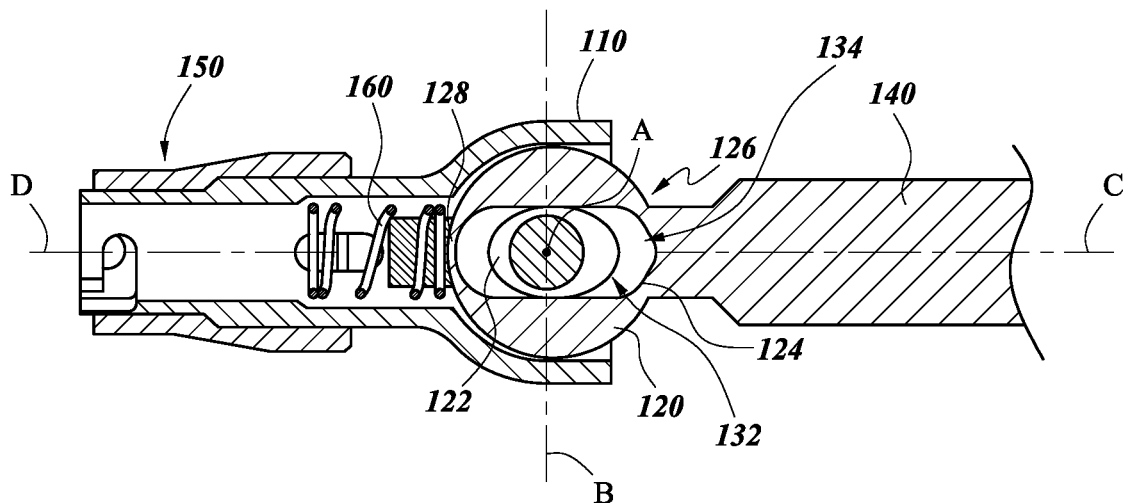
FIGS. 3A and 3B depict cross-sectional views of the universal joint shown in FIG. 2A taken along line 3-3, in accordance with an illustrative embodiment, where

FIG. 2A shows the universal joint assembly 100 with the pin 130 extending vertically. FIG. 3A shows a cross-sectional view taken along the line 3-3 in FIG. 2A. As illustrated in FIG. 1, the ball 120 includes a proximal end 126 and a distal end 128. In some embodiments, the ball 120 is generally spherical. In some embodiments, the ball 120 is at least partially spherical. In some embodiments, the surface of the ball 120 includes at least one flat portion. In some embodiments, the distal end 128 of the ball 120 has a partially flat surface. As illustrated in FIG. 3A, the ball 120 includes an opening 122 that extends through the ball 120. In some embodiments, the opening 122 may extend through the center of the ball 120, as shown in FIG. 3A. In some embodiments, the opening 122 may be off-centered.

FIG. 4A depicts a top view of the ball 120, pin 130, and drive shaft 140, showing the shape of opening 122. As illustrated in FIGS. 1 and 4A, the opening 122 may be defined by an edge 124, which extends from a proximal edge 125 to a distal edge 127. In some embodiments, the edge 124 may extend from the center of the ball 120 towards at least one end of the ball 120. As illustrated in FIGS. 1 and 4A, the edge 124 may extend from the center of the ball 120 towards the proximal and distal ends 126, 128 of the ball 120. In some embodiments, the edge 124 may extend only towards the proximal end 126. In some embodiments, the edge 124 may extend only towards the distal end 128. In some embodiments, the proximal edge 125 of the opening 122 may extend completely to the proximal end 126 of the ball 120. In other embodiments, the proximal edge 125 of the opening 122 may extend partially towards the proximal end 126. In some embodiments, the distal edge of the opening 122 may extend completely to the distal end 128 of the ball 120. In other embodiments, the distal edge 127 of the opening 122 may extend partially towards the distal end 128 of the ball 120. In some embodiments, at least one of the proximal and distal edges 125, 127 are curvilinear surfaces. In some embodiments, at least one of the proximal and distal edges 125, 127 are generally flat surfaces.

In some embodiments, the width of the distal edge 127 is substantially similar to the width of the proximal edge 125. In other embodiments, the width of the distal edge 127 is greater than or less than the width of the proximal edge 125. In some embodiments, the width of at least one of the proximal and distal edges 125, 127 is narrower than at the center of the opening 122. In some embodiments, the width of the opening 122 is narrower at the center of the opening than at least one of the proximal and distal edges 125, 127.

In some embodiments, the width of the of the opening 122 is substantially similar through the ball 120. In some embodiments, the width of the opening 122 is wider at the edge 124 than at an interior of the opening 122. In some embodiments, the width of the edge 124 of the opening 122 is narrower than at an interior of the opening 122.

In some embodiments, the opening may have more than one edge 124. In some embodiments, the ball 120 may have two edges 124 that are on opposite sides of the ball 120. In some embodiments, the edges 124 may have substantially similar shapes. In some embodiments, the edges 124 may have different shapes.

In some embodiments, the ball 120 is made from stainless steel, titanium, tungsten carbide, ceramic, composite material, or the like.

The ball 120 may be coupled to a drive shaft 140, as illustrated in FIGS. 1-4B. The drive shaft 140 includes a distal end 142 and a proximal end 144. In some embodiments, the proximal end 144 of the drive shaft 140 may be coupled to a surgical power gun. In some embodiments, the proximal end 144 of the drive shaft 140 may be coupled to a handle. The distal end 142 of the drive shaft 140 may be coupled to the proximal end 126 of the ball 120. The distal end 142 of the drive shaft 140 may be coupled to the proximal end 126 of the ball 120 via welding, adhesive, snap-fit, pin, etc. In some embodiments, the ball 120 and the drive shaft 140 are an integral piece. In some embodiments, the drive shaft 140 is a rigid material, such as stainless steel, tungsten carbide, titanium, ceramic, hard plastic, composite material or the like.

As illustrated in FIGS. 3A-B and 4A-B, the pin 130 extends through the opening 122 in the ball 120. The length of the pin 130 may be longer than the diameter of the ball 120, such that the pin 130 extends past the exterior surface 123 of the ball 120. The socket 110 is configured to receive the ball 120 and pin 130. In some embodiments, the socket 110 is made from stainless steel, titanium, tungsten carbide, ceramic, composite material, hard plastic, polymer, or the like. In some embodiments, the pin 130 is made from stainless steel, titanium, tungsten carbide, ceramic, composite material, polymer, hard plastic, or the like. In some embodiments, the socket 110 includes a liner material that contacts the ball 120.

Figure 3B:
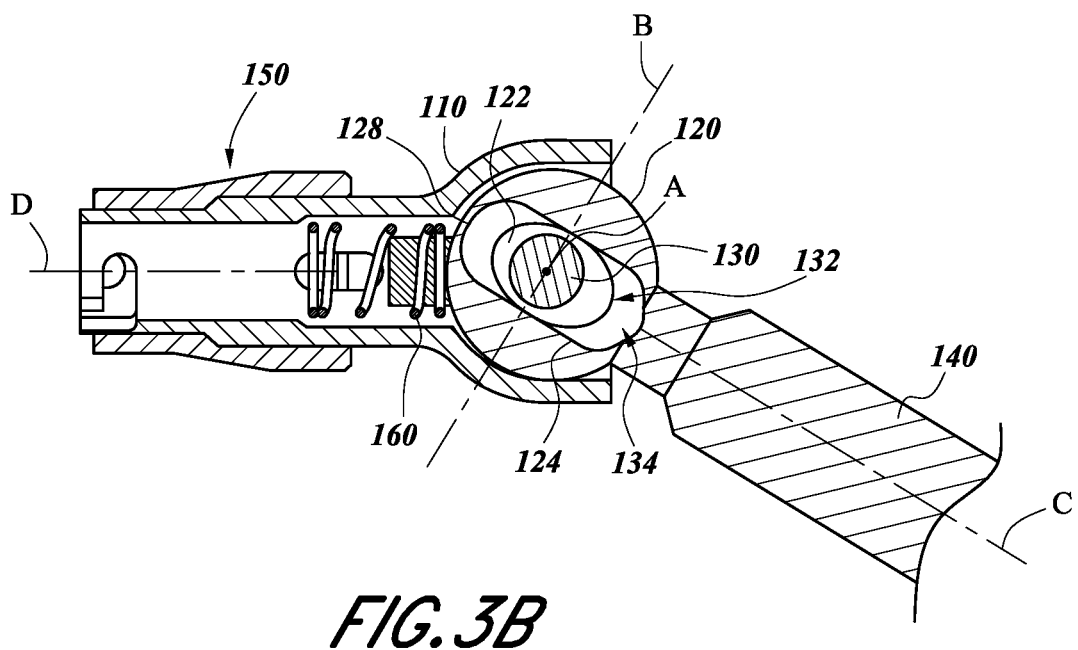

The ball 120 is coupled to the socket 110 via the pin 130, as illustrated in FIG. 1. The pin 130 includes a longitudinal axis A that extends parallel to the length of the pin 130. FIG. 3A depicts the ball 120 and drive shaft 140 in a first position. FIG. 3B depicts the ball 120 drive shaft 140 in a second position, rotated about the longitudinal axis A of the pin 130. The ball 120 and drive shaft 140 are rotatable clockwise and counterclockwise around the longitudinal axis A of the pin 130. As shown in FIG. 3B, the ball 120 and drive shaft 140 are rotated in the clockwise direction. The socket 110 limits the rotation of the ball 120 and drive shaft 140. In some embodiments, the socket 110 may be configured to limit the rotation of the ball 120 to a certain degree.

Figure 2B:
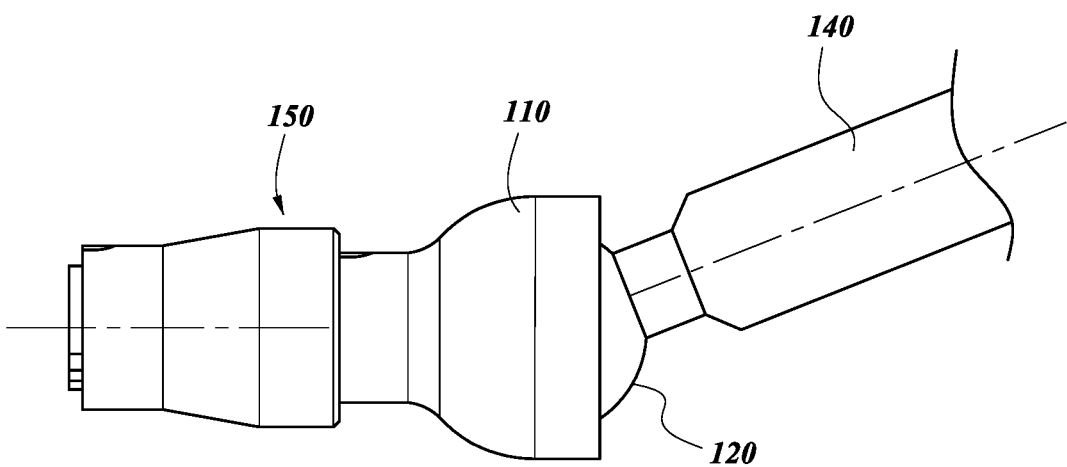

The ball 120 and drive shaft 140 are rotatable about an axis that is perpendicular to the longitudinal axis A of the pin 130. FIG. 2A depicts the ball 120 and drive shaft 140 in a third position and FIG. 2B depicts the ball 120 and drive shaft 140 in a fourth position. The ball 120 and drive shaft 140 are rotatable between the third and fourth position about an axis B (as illustrated in FIG. 4B) that is perpendicular to the longitudinal axis A of the pin 130 (e.g., in FIG. 4B the axis B is normal to the sheet). The ball 120 and drive shaft 140 may be rotatable inside the socket 110 about the intersection point between the two axis.

The position of the ball 120 may be fixed by an biasing (elastic) mechanism 160, which may include one or more components. In various embodiments, the biasing mechanism 160 may include a spring, rubber, silicone, polymer, or the like. The biasing mechanism 160 may be biased to exert pressure on the ball 120 in at least one direction. In some embodiments, the elastic mechanism 160 may exert pressure on the ball 120 in the proximal direction. As illustrated in FIG. 1, the biasing mechanism 160 may be coupled to the socket 110 via a pin 162. In some embodiments, the biasing mechanism 160 may be coupled to the socket 110 via welding, adhesive, screws, or the like. In some embodiments, the biasing mechanism 160 may be integral with the socket 110.

Figure 5:
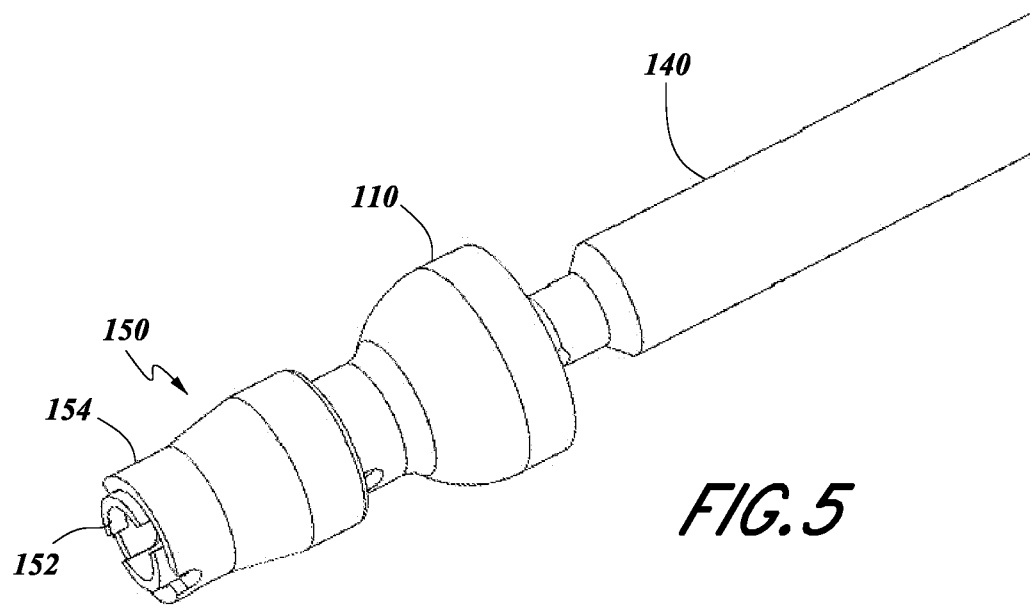
FIG. 5 depicts a perspective view of the universal joint with an outer fitting component.
Figure 6:
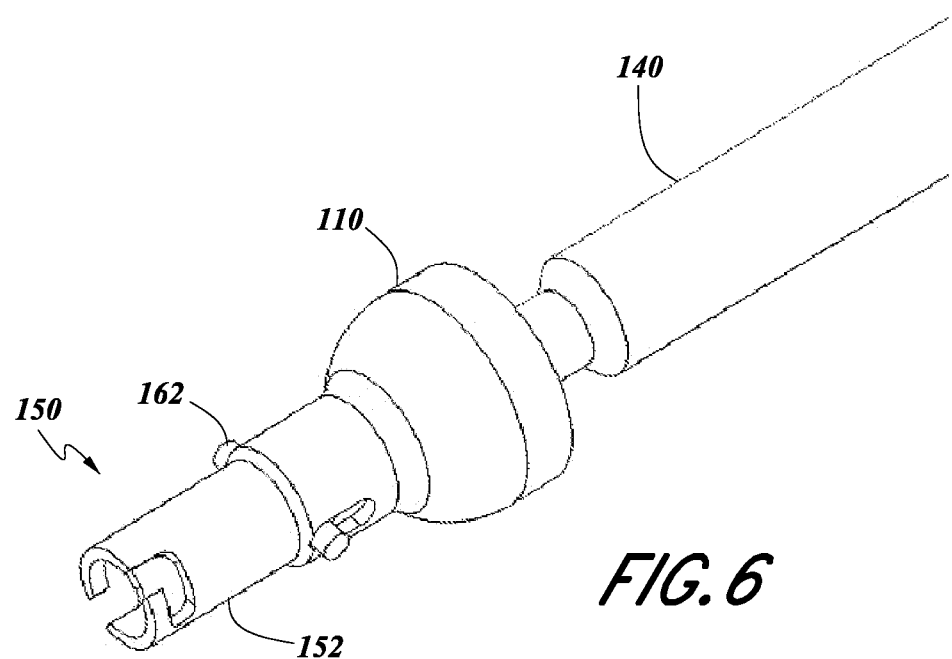
FIG. 6 depicts a perspective view of the universal joint with the outer fitting component removed.

FIGS. 5 and 6 depict the fitting 150 in accordance with certain embodiments. In some embodiments, the fitting 150 may include an inner component 152 and an outer component 154. FIG. 5 shows the fitting 150 with an outer component 154, while FIG. 6 shows the fitting 150 with the outer component 154 removed. In some embodiments, the outer component 154 may be coupled to the inner component 152 via pin 162, as illustrated in FIGS. 5 and 6. In some embodiments, the inner and outer components 152, 154 may be coupled via snap-fit, threads, welding, adhesive, or the like. The fitting 150 is coupled to the socket 110. In some embodiments, at least a portion of the fitting is integral with the socket 110. In some embodiments, the fitting 150 is coupled to the socket 110 via welding, adhesive, pin, screw, or the like. As illustrated in FIG. 3A, the inner component 152 is integral with the socket 110. In other embodiments, the fitting 150 is separate and distinct from the socket 110. In some embodiments, the fitting 150 may include a surgical tool, such as drill bit, screw driving feature, or the like. In some embodiments, the fitting 150 may include a modular connection or quick connect fitting. In some embodiments, the quick connect fitting may couple to a surgical tool, such as a drill bit, screw driving feature, or the like.

In some embodiments, the universal joint assembly 100 includes a drive shaft 140 and a fitting 150. In some embodiments, the fitting 150 may be in a position where it is rotated about the longitudinal axis A of the pin 130 and it is rotated about the axis B that is perpendicular to the longitudinal axis A of the pin 130. This allows for the angle of the fitting 150 to be adjusted to different angles with respect to the drive shaft 140 in at least two dimensions. The drive shaft 140 is rotatable about its longitudinal axis C (as illustrated in FIG. 4B). In some embodiments, the longitudinal axis C of the drive shaft 140 may be perpendicular to a plane defined by the longitudinal axis A of the pin 130 and the axis B that is perpendicular to the longitudinal axis A of the pin 130. Rotation of the drive shaft 140 may cause rotation of the pin 130 and socket 110 and consequently rotation of the fitting 150 about its longitudinal axis D (depicted as dotted lines in FIGS. 2A and 2B and 3A-B). The pin 130 may transmit torque between the socket 110 and the ball 140 to rotate the fitting 150. In some embodiments, as illustrated in FIGS. 2B and 3B, the fitting 150 may rotate when the fitting 150 is oriented at an angle to the drive shaft 140. Longitudinal axis A shown in FIG. 4 is referred to as a first longitudinal axis; longitudinal axis B shown in FIG. 4B is referred to as a second longitudinal axis; longitudinal axis C shown in FIG. 4B is referred to as a third longitudinal axis; longitudinal axis D shown in FIGS. 3A and 3B is referred to as a fourth longitudinal axis.

Figure 7:
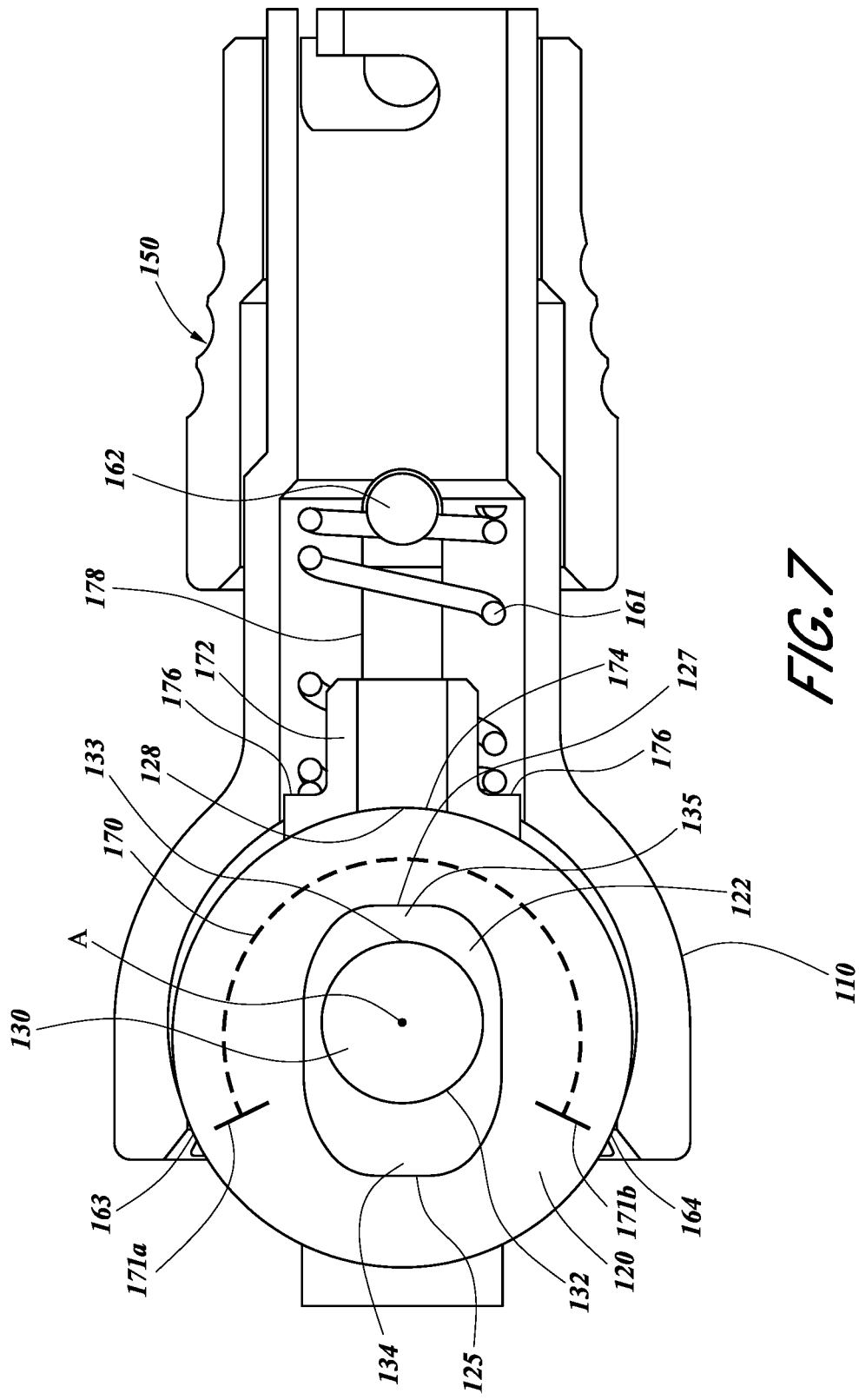
FIG. 7 depicts a cross-sectional side view of the universal joint shown in FIG. 1.
Figure 8:
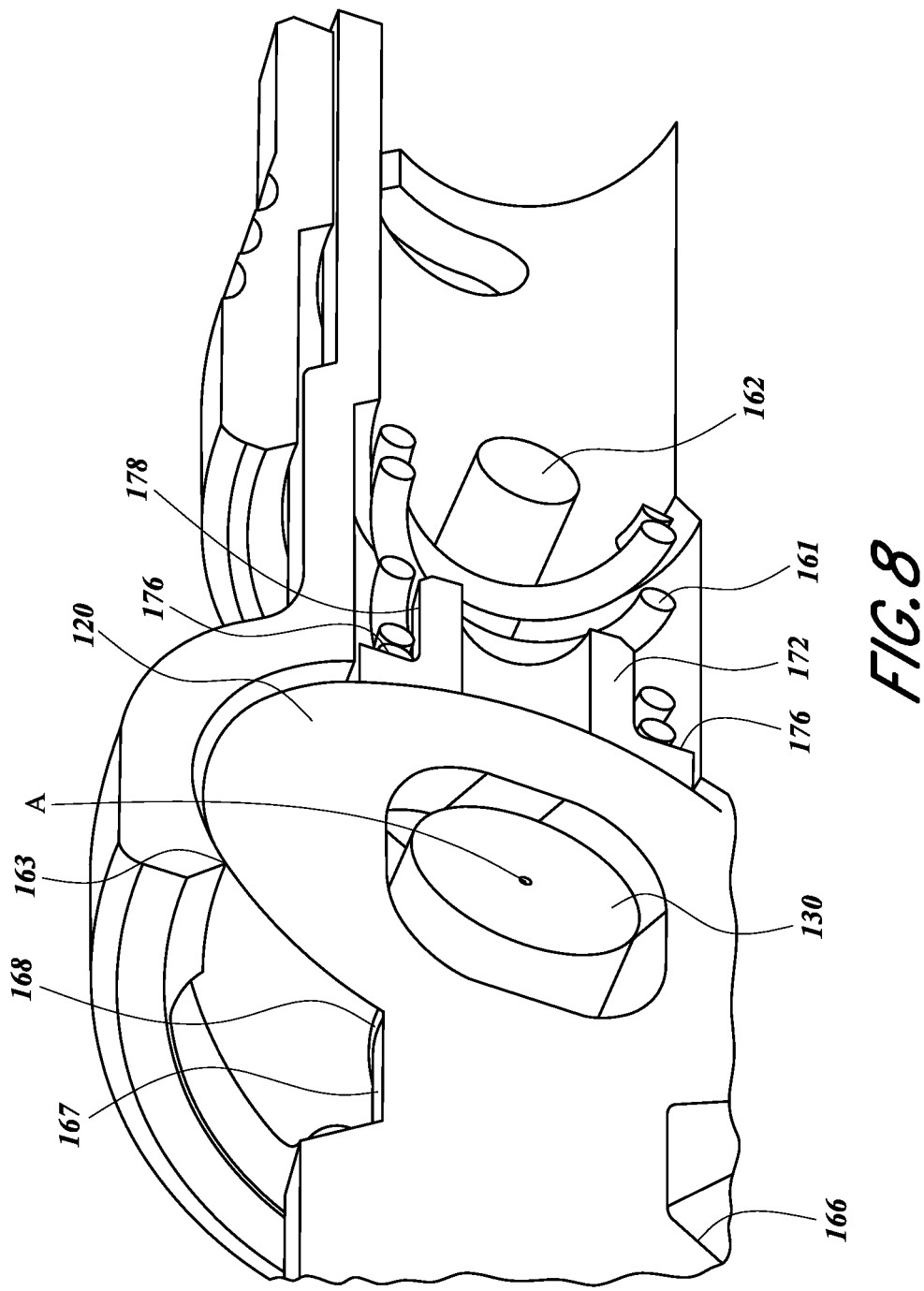
FIG. 8 depicts a cross-sectional perspective side view of the universal joint shown in FIG. 1.

FIG. 7 depicts a cross-sectional side view of an example of the universal joint. FIG. 8 depicts a cross-sectional perspective side view of an example of the universal joint shown in FIG. 7. The universal joint shown in FIGS. 7 and 8 includes a ball 120 positioned in a socket (housing) 110, and includes features as illustrated in FIGS. 1-6. In the example of FIG. 7, the socket 110 extends around the ball 120 further than the socket 110 extends around the ball 120 in FIGS. 1-6. That is, the socket 110 in FIG. 1-6 extends about half-way around the ball 120, such that the socket 110 extends about 180° around the ball 120. In FIGS. 7 and 8, the socket 110 extends more than 180° around the ball 120 such that the socket 110 extends more than half-way around the ball 120. In this embodiment, when the driveshaft portion (the left-side of the universal joint illustrated in FIG. 7) is moved vertically such that the ball 120 rotates clockwise in relative to the orientation in FIG. 7, the ball 120 can be rotated clockwise until a distal end 168 of the driveshaft (FIG. 8) contacts a first edge 163 of the socket 110. Similarly, when the ball 120 is rotated counterclockwise and relative to the orientation in FIG. 7, the ball 120 can be rotated counterclockwise and told distal end 163 of the driveshaft (FIG. 8) contacts a second edge 164 of the socket 110.

In FIG. 7, indicator 170 illustrates the extent that the socket 110 surrounds the ball 120. A first side 171a of indicator 170 is aligned with the first edge 163 of the socket 110. A second side 171b of indicator 170 is aligned with the second edge 164 of the socket 110. The indicator 170 thus illustrates the extension of the socket 110 around the ball 120 of more than 180°. In various embodiments, the extension of the socket 110 around the ball 120 may be greater than 180°. In various implementations, the extension of the socket 110 around the ball 120 may be, for example, just over 180°, at about 181°, 182°, 183°, 184°, 185°, 186°, 187°, 188°, 189°, or 190°. In some implementations, the extension of the socket 110 around the ball 120 may be greater than 190°. For example, at about between 190° and 195°, between 194° and 200°, between 199° and 205°, between 204° and 210°, between 209° and 215°, between 214° and 220°, between 219° and 225°, between 224° and 230°, or greater than 230°. Implementations with the socket 110 surrounds a greater part of the ball 120 may provide for a more secure fit of the ball 120 into the socket 110, and allow the ball 120 to press up against a larger portion of the socket 110 that surrounds the ball 120 when the contact surface 174 of the biasing mechanism 160 is pushing against the distal end 128 of the ball 120. In some implementations, having the socket 110 extend around the ball 120 a greater amount can make it more difficult to place the ball inside the socket 110. For example, if the socket is less flexible. In some limitations, depending on the strength of the biasing mechanism 160 it can be advantageous to have the socket 110 extend further around the ball 120.

During a surgical procedure, such as total hip replacement, the surgical area may be tight. In order to correctly position the screws for the acetabular cup implant, the fitting 150 may need to be positioned at a certain angle to the drive shaft 140. To adjust the positioning of the universal joint assembly 100, a user may rotate the ball 120 about the longitudinal axis A of the pin 130 or about the axis B that is perpendicular to the longitudinal axis A of the pin 130. In some embodiments, the user may simultaneously rotate the ball 120 about the longitudinal axis A and the perpendicular axis B. Once the ball 120 is positioned, the user may fix its position via the elastic mechanism 160.

In some embodiments, a user couples the fitting 150 to a surgical tool, such as a drill bit, screw driving feature, saw, or the like. In some embodiments, the fitting 150 is a surgical tool. In some embodiments, a user couples the drive shaft 140 to a handle. In some embodiments, a user couples the drive shaft 140 to a power supply, such as a surgical gun. The user may use the surgical gun to rotate the drive shaft 140 at high RPMs, which in turn rotates the fitting 150. In some embodiments, a surgeon may use the universal joint assembly 100 to drill a pilot hole or insert a screw during a hip replacement surgery.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Headings are included herein for reference and to aid in locating various sections. These headings are not intended to limit the scope of the concepts described with respect thereto. Such concepts may have applicability throughout the entire specification.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

The phrase "based on" does not mean "based only on," unless expressly specified otherwise. In other words, the phrase "based on" describes both "based only on" and "based at least on." Unless otherwise explicitly stated, articles such as "a" or "an" should generally be interpreted to include one or more described items. Accordingly, phrases such as "a device configured to" are intended to include one or more recited devices.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. A surgical device, comprising:
a socket having a housing;
a drive shaft extending in a longitudinal direction;
a ball coupled to the drive shaft, the ball disposed at least partially in the socket and configured to rotate within the socket, the ball comprising an elongated opening extending through the ball, the elongated opening having a cross-sectional area in the interior of the ball smaller than a cross-sectional area at the surface of the ball, a perimeter of the elongated opening extending in a longitudinal direction that is aligned with the longitudinal direction of the drive shaft;
a first pin coupled to the socket and disposed at least partially in the socket, the first pin comprising a first longitudinal axis and extending through the elongated opening of the ball between opposite sides of the socket;
a biasing mechanism biased to exert a force on the ball, the biasing mechanism coupled to the socket and a contact component positioned between the ball and the biasing mechanism, the contact component having a surface that contacts the ball; and
wherein the ball is configured to partially rotate about the first longitudinal axis of the first pin, and partially rotate about a second axis perpendicular to the first longitudinal axis of the first the pin, in a plane aligned with the elongated opening.

2. The surgical device of claim 1, wherein the biasing mechanism comprises a spring.

3. The surgical device of claim 2, wherein the contact component is positioned between the ball and the spring.

4. The surgical device of claim 1, wherein the socket further comprises an aperture, and wherein the ball and the pin are positioned partially in the aperture.

5. The surgical device of claim 1, wherein the ball comprises titanium.

6. The surgical device of claim 1, wherein the ball comprises stainless steel.

7. The surgical device of claim 1, wherein the ball comprises tungsten carbide.

8. The surgical device of claim 1, wherein the ball comprises ceramic.

9. The surgical device of claim 1, wherein the ball comprises a composite material.

10. The surgical device of claim 1, wherein the drive shaft defines a third longitudinal axis, and the ball is rotatable about the third longitudinal axis.

11. The surgical device of claim 10, wherein the third longitudinal axis of the drive shaft is perpendicular to a plane defined by the first longitudinal axis of the first pin and the second axis.

12. The surgical device of claim 10, wherein the biasing mechanism is configured to exert a bias force on the ball via the contact component in a direction along a fourth longitudinal axis.

13. The surgical device of claim 12, further comprising a fitting coupled to the socket, wherein the fitting is configured to rotate about the fourth longitudinal axis of the fitting.

14. The surgical device of claim 13, wherein the fitting is a quick connect fitting configured to couple to a tool.

15. The surgical device of claim 14, wherein the tool is a surgical drill bit or a screwdriver.

16. The surgical device of claim 1, wherein the drive shaft is integral with the ball.

17. The surgical device of claim 1, wherein a rotation of the drive shaft about the first longitudinal axis of the first pin moves the drive shaft from a first position and a second position.

18. The device of claim 1, wherein a rotation of the drive shaft about the second axis moves the drive shaft from a third position to a fourth position.

* * * * *